(12) United States Patent
Vogel et al.

(10) Patent No.: US 7,188,750 B2
(45) Date of Patent: Mar. 13, 2007

(54) BLOW FILL SEALED CONTAINER WITH TWIST OFF TOP OPERATED BY OVERCAP AND METHOD OF FORMING THE SAME

(75) Inventors: James E. Vogel, Libertyville, IL (US); Jeffery Setesak, Lincolnshire, IL (US); Gregory G. Pieper, Waukegan, IL (US)

(73) Assignee: Hospira, Inc., Lake Forest, IL (US)

( * ) Notice: Subject to any disclaimer, the term of this patent is extended or adjusted under 35 U.S.C. 154(b) by 272 days.

(21) Appl. No.: 10/655,718

(22) Filed: Sep. 5, 2003

(65) Prior Publication Data
US 2005/0051572 A1    Mar. 10, 2005

(51) Int. Cl.
B67B 5/00 (2006.01)
B65D 47/10 (2006.01)

(52) U.S. Cl. ............... 222/83; 222/153.07; 222/541.2; 215/48

(58) Field of Classification Search .............. 222/81, 222/82, 83, 153.05, 153.06, 153.07, 541.2; 215/48
See application file for complete search history.

(56) References Cited

U.S. PATENT DOCUMENTS

| | | | |
|---|---|---|---|
| 4,134,511 A | 1/1979 | Deussen | |
| 4,463,878 A * | 8/1984 | Crone | 222/153.06 |
| 4,527,700 A | 7/1985 | Jupin et al. | |
| 4,620,638 A | 11/1986 | Schmidt | |
| 4,643,309 A | 2/1987 | Evers | |
| 5,158,192 A | 10/1992 | Lataix | |
| 5,228,593 A | 7/1993 | O'Meara | |
| 5,409,125 A | 4/1995 | Kimber et al. | |
| 5,419,459 A * | 5/1995 | O'Meara | 222/83 |
| 5,425,920 A | 6/1995 | Conti et al. | |
| 5,813,570 A * | 9/1998 | Fuchs et al. | 222/82 |
| 6,000,578 A * | 12/1999 | Boissay | 222/83 |
| 6,126,045 A * | 10/2000 | Last | 222/501 |
| 6,321,942 B1 * | 11/2001 | Krampen et al. | 222/82 |
| 2002/0035820 A1 | 3/2002 | Farris | |
| 2002/0128612 A1 | 9/2002 | Andersson et al. | |
| 2003/0032923 A1 | 2/2003 | Eakins et al. | |

* cited by examiner

Primary Examiner—Joseph A. Kaufman
(74) Attorney, Agent, or Firm—Michael R. Crabb

(57) ABSTRACT

A container assembly includes a container body having a port or aperture adapted for use with a luer end of a needleless syringe. The aperture is sealed to a closure top by a first frangible seal. An overcap has a cap base sealed to the container body and an upper cap connected to the cap base by a second frangible seal, providing a sterile barrier surrounding the first frangible seal. The second frangible seal is broken by depressing the upper cap toward the container body. Alternatively, the second frangible seal is a removable tear strip broken by tugging on the tear strip. The upper cap includes a detent portion frictionally securing the upper cap to the closure top when the upper cap is depressed toward the container body. The upper cap and secured closure top are removed from container body by twisting the upper cap to break the first frangible seal and open the port.

8 Claims, 6 Drawing Sheets

BLOW FILL SEALED CONTAINER WITH TWIST OFF TOP OPERATED BY OVERCAP AND METHOD OF FORMING THE SAME

The present invention relates to the field of containers. More particularly this invention relates to a sterile container assembly for storing fluids, including but not limited to drugs, and transferring them to a needleless syringe.

BACKGROUND OF THE INVENTION

In the past, the general practice of surgeons or other medical practitioners using hypodermic syringes has been to transfer an injection solution to a syringe from ampoules or vials holding a single dose. These ampoules have been adapted to be sealed by a non-resealable cap. The ampoule is opened by rocking the non-resealable cap, tearing the non-resealable cap from an outlet of the ampoule at an area of weakness.

The outlets of these ampoules are often designed to mate with the open end of a needleless syringe. The open ends of needleless syringes come in several different forms or shapes. The two most popular forms of needle fitting are the friction fit fitting (such as the luer slip fitting) and the combination of screw thread and friction engagement fitting (such as the luer lock fitting). Ampoules with outlets that are designed to mate with luer slip fittings and ampoules with outlets that are designed to mate with luer lock fittings are known.

It will be appreciated that this past practice has required separate sterilizing measures, as solution transfer for injecting into humans requires scrupulous sterilizing of components.

Prior solutions for keeping these ampoules sterile include utilization of blister packaging of the ampoules prior to sterilization. This blister packaging is both costly and difficult to remove.

Other types of conventional containers have a cover that the user turns to engage the cap and tear the cap from the container. None of these containers are adapted to operate with a needleless syringe. Further, none of these containers are particularly well adapted to prevent compromise or contamination of the sterile port of the container during the manual manipulation required to open the port.

Therefore, a principal object of this invention is to provide a container assembly that maintains a sterile attachment zone for a needleless syringe.

Another object of the invention is to provide a container assembly that has a guarded sterile syringe attachment zone, which is easily compromised during the manual manipulation, required to open the container assembly.

Another object reduces risk of contamination of its opened port by finger touches.

Another object of the invention is to provide a container assembly adapted for use with a needleless syringe and which includes an overcap to facilitate removal of a closure top from the container.

A further object of the invention is to provide an overcap with an improved detent portion for engaging the closure top of a container.

These and other objects will be apparent to those skilled in the art.

SUMMARY OF THE INVENTION

A container assembly includes a container body having a port adapted for use with a luer end of a needleless syringe. A first frangible seal seals the aperture to a closure top. An overcap has a cap base sealed to the container body and an upper cap connected to the cap base by a second frangible seal, providing a sterile barrier surrounding the first frangible seal. Depressing the upper cap toward the container body breaks the second frangible seal. Alternatively, the second frangible seal is a removable tear strip broken by tugging on the tear strip. The upper cap includes a detent portion frictionally securing the upper cap to the closure top when the upper cap is depressed toward the container body. The upper cap and secured closure top are removed from container body by twisting the upper cap to break the first frangible seal. After removal, the top remains frictionally retained in the upper cap by the detent portion.

DESCRIPTION OF THE PREFERRED EMBODIMENT

Figure 1:
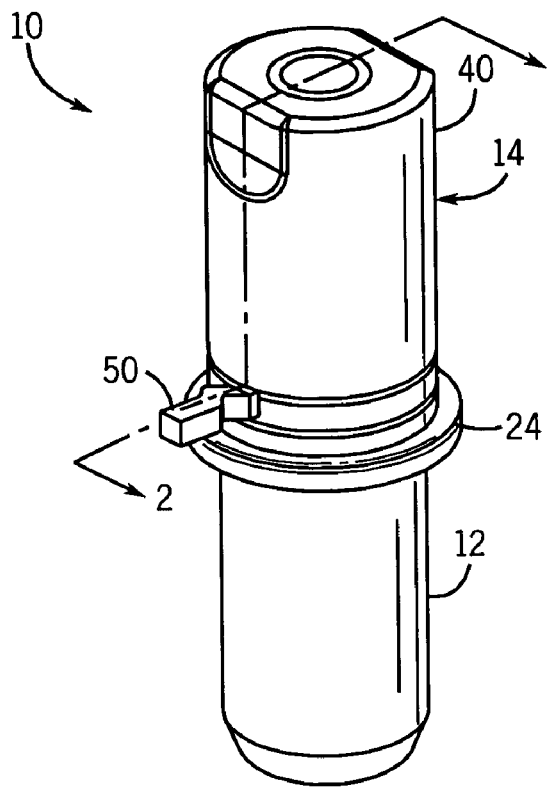
FIG. 1 is a perspective view of the device of this invention.

With reference to FIG. 1, a container assembly 10 includes a container body 12 for containing fluid, including but not limited to drugs. An overcap 14 is sealed to the container body 12 to provide a barrier over a portion of the container body 12 to prevent contamination by touch or otherwise. The overcap 14 provides a sterile barrier once the entire container assembly 10 has been sterilized.

Figure 2:
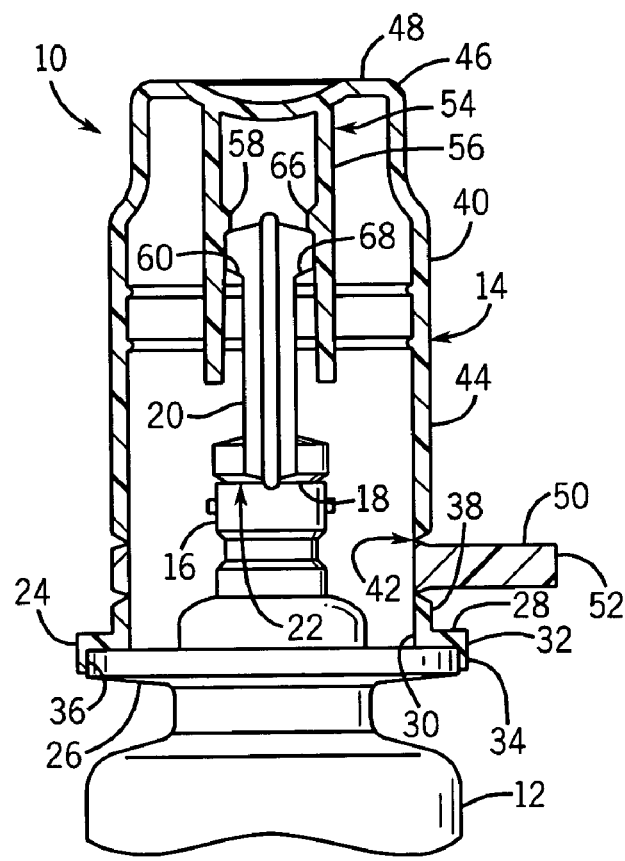
FIG. 2 is a partial sectional side view of the device of this invention taken on line 2—2 of FIG. 1.

Referring to FIG. 2, a port 16 provides access to the contents of the container body 12 through an aperture 18. A non-resealable closure top 20 is sealed over the aperture 18 to the container body 12 at a first frangible seal 22. The first frangible seal 22 is a sterilized surface, where the overcap 14 is positioned over the first frangible seal 22 and sealed to the container body 12 to provide a sterile barrier or zone surrounding the first frangible seal 22.

A cap base 24 of overcap 14 is sealed to a horizontally extending flange 26 on the container body 12. The cap base 24 has a horizontally extending lip 28 with an outer end 30 and an inner end 32. An annular skirt 34 extends downwardly from the outer end 30 and mates with an outer edge 36 of flange 26 on the container body 12. An annular rim 38 extends upwardly from the inner end 32 of lip 28.

Figure 3:
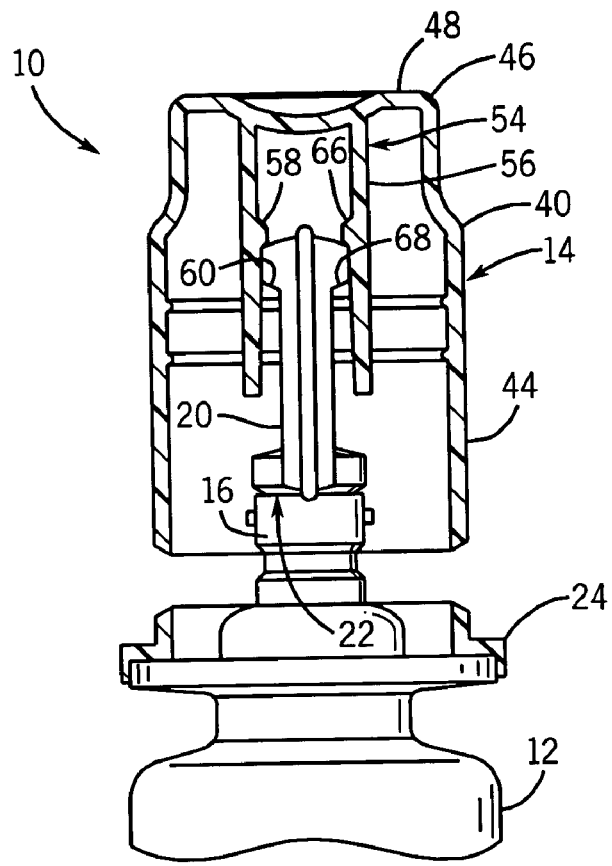
FIG. 3 is a partial sectional side view similar to FIG. 2, but the tear strip has been removed.

Referring to FIGS. 2 and 3, an upper cap 40 of overcap 14 is sealed to the cap base 24 by a second frangible seal 42. A cylindrical skirt portion 44 of upper cap 40 extends downwardly from an outer portion 46 of a radial extending end 48. The second frangible seal 42 seals the cylindrical skirt 44 to the cap base 24.

A removable tear strip 50 is located between the annular rim 38 of cap base 24 and the cylindrical skirt portion 44 of upper cap 40, forming the second frangible seal 42. The tear strip 50 has a hold area 52 that extends horizontally from the overcap 14. The hold area 52 permits a user to grasp and pull the hold area 52 to remove the tear strip 50. When tear strip 50 is removed the second frangible seal 42 is broken and the cap base 24 and upper cap 40 are severed from each other.

Figure 4:
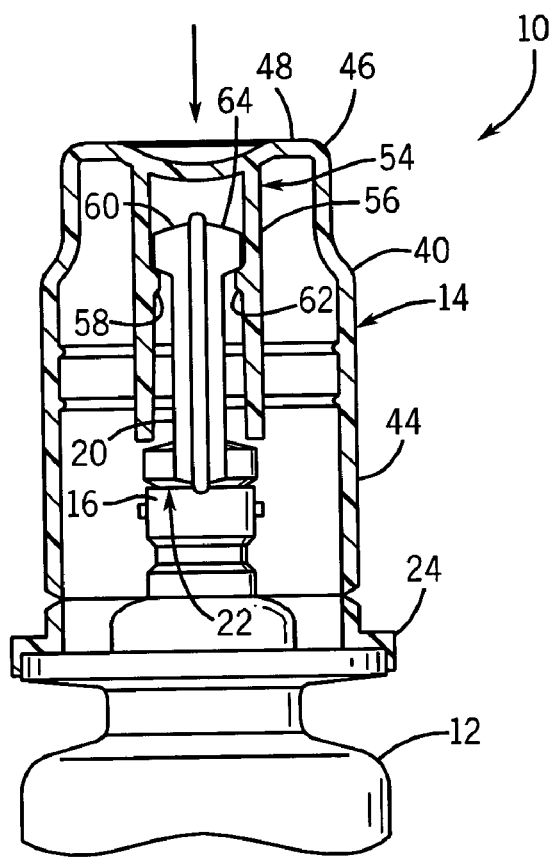
FIG. 4 is a partial sectional side view similar to FIG. 3, but the upper cap has been pressed downward to retentively engage the closure top.

Referring to FIGS. 3 and 4, a detent portion 54 of upper cap 40 frictionally attaches the closure top 20 to the upper cap 40 once the second frangible seal 42 (not shown) is broken. Once the second frangible seal 42 (not shown) is broken by removing the tear strip 50 (not shown), the upper cap 40 is depressed towards the container body 12, mating the detent portion 54 to the closure top 20.

The detent portion 54 includes planar finger elements 56 extending downwardly from the end 48 of upper cap 40 and around the closure top 20. Each finger element 56 includes a finger shoulder 58 mateable with a corresponding tang shoulder 60 on the closure top 20.

Some force is required to move a bottom edge 62 of the finger shoulder 58 over a leading edge 64 of the tang shoulder 60. Once the upper cap 40 is depressed, a top edge 66 of the finger shoulder 58 contacts a trailing edge 68 of the tang shoulder 60, preventing the closure top 20 from detaching from the detent portion 54. Although various mating configurations are possible, preferably the finger shoulder 58 and the tang shoulder 60 both extend horizontally.

Figure 5:
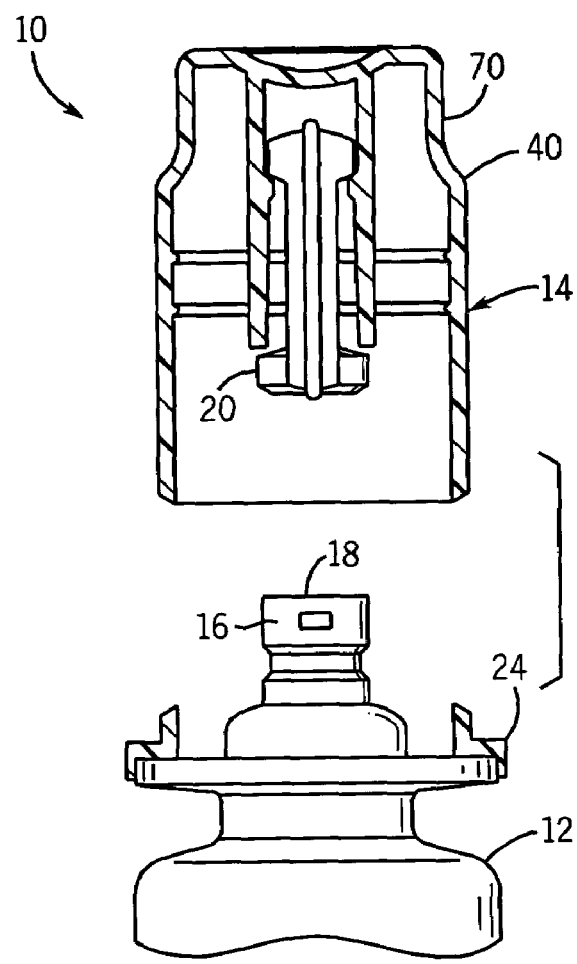
FIG. 5 is a partial sectional side view similar to FIG. 4, but the overcap and the closure top retained therein have been removed.

Referring to FIG. 5, a grip area 70 is located the outer surface of upper cap 40. The grip area 70 permits a user to grasp and rotate the upper cap 40. As the upper cap 40 is rotated, the mated detent portion 54 and closure top 20 twist relative to the container body 12. This rotation breaks the first frangible seal 22 (not shown). Once the first frangible seal 22 (not shown) is broken, the detent portion 54 and closure top 20 remain mated, and are removed from the container body 12. The closure top 20 is retained within the upper cap 40 once removed from the container body 12.

The upper cap 40 provides a balanced application of torque resulting in a clean break of the first frangible seal 22 (not shown). This clean break minimizes the amount of plastic strands generated from the broken seal.

Figure 6:
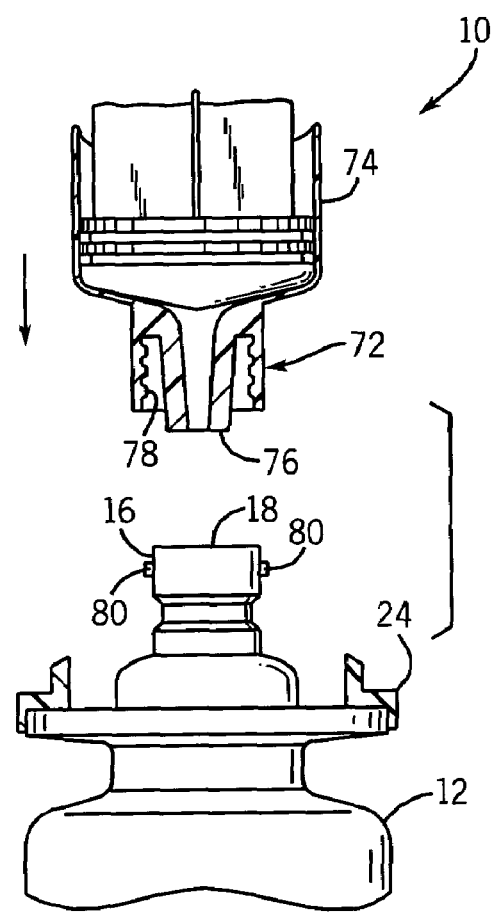
FIG. 6 is a partial sectional front view of a syringe and the opened container of this invention.

Referring to FIG. 6, a luer end 72 of a syringe 74 is inserted into the aperture 18 of port 16 once the closure top 20 is removed. The syringe 74 allows a user to extract fluid content from the container 12. The luer end 72 is shown as a luer lock fitting but may be a luer slip fitting. The luer end 72 includes a male luer 76 and a female threaded surface 78. The male luer 76 is inserted into the aperture 18 of the port 16. The female threaded surface 78 is engaged to port threads 80 located on the port 16 to threadingly mate the luer end 72 to the port 16.

Referring to FIGS. 7 through 12, a second embodiment of the present invention includes an upper cap 82 sealed to the cap base 24 by a second frangible seal 84. A cylindrical skirt portion 86 extends downwardly from a rectangular detent portion 88 of upper cap 82. The cylindrical skirt 86 is located within the cap base 24 and is sealed to the cap base 24 by the second frangible seal 84. The second frangible seal 84 can be broken by manually depressing the upper cap 82 toward the container body 12, whereupon the detent portion 88 of upper cap 82 frictionally attaches to a closure top 90. Alternatively, the user can rock the upper cap 82 back and forth until the second frangible seal 84 fractures, then push the upper cap 82 downward.

The detent portion 88 includes substantially planar surface elements 92 extending upwardly from cylindrical skirt portion 86 of upper cap 82 and positioned around the closure top 90. Each substantially planar surface element 92 corresponds to a corresponding substantially planar surface portion 94 of closure top 90. One or more optional friction enhancing elements 95 are formed in one or more of the substantially planar surface elements or portions 92, 94. The friction enhancing elements 95 are shown as a pair of raised domes on the substantially planar surface portions 94; however, those skilled in the art will understand from the description herein that other friction enhancing elements or combinations of elements can be utilized, including but not limited to ribs, ribs and grooves, and other complementary or noncomplementary surface irregularities, without detracting from the present invention. At any rate, the substantially planar surface elements 92 and the substantially planar surface portions 94 are configured so that some force is required to retentively engage planar surface elements 92 to the planar surface portions 94. Once the upper cap 82 is depressed, the planar surface elements 92 frictionally engage the planar surface portions 94, preventing the closure top 90 from detaching from the detent portion 88.

Figure 7:
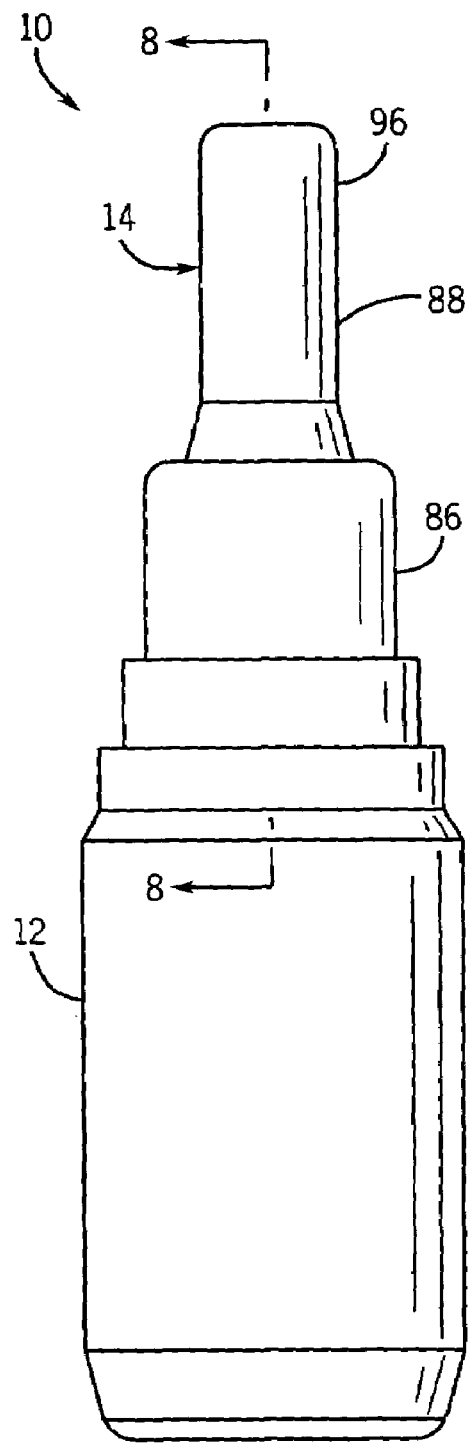
FIG. 7 is a side view of a second embodiment of the device of this invention.
Figure 10:
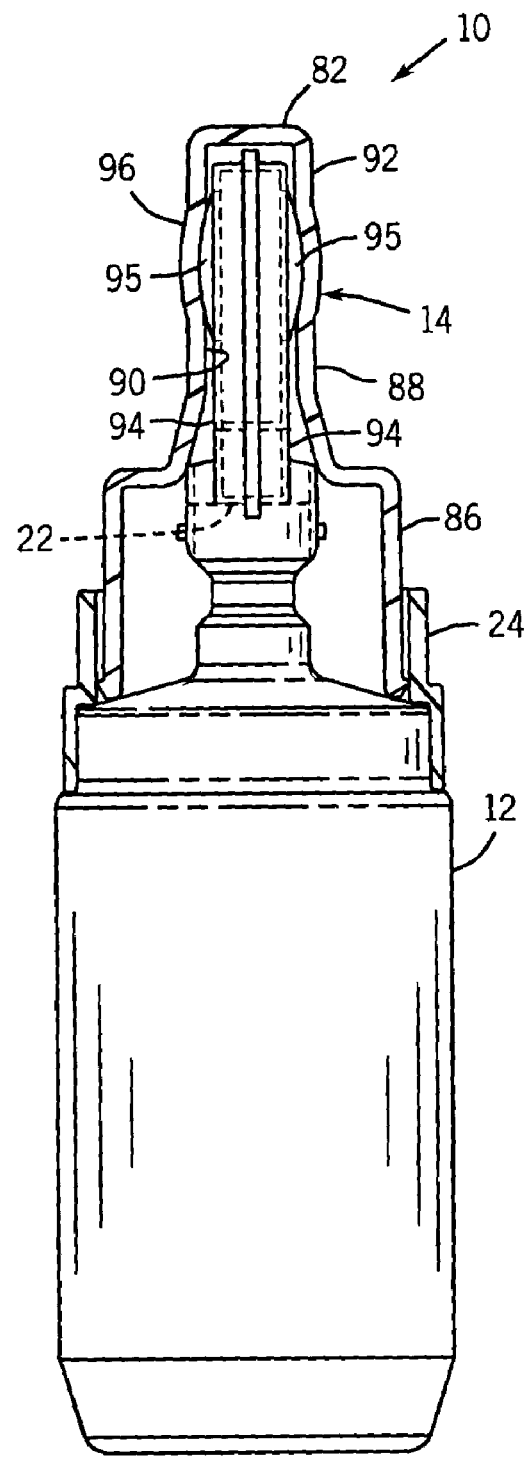
FIG. 10 is a partial sectional side view of the device of this invention taken on line 10—10 of FIG. 9.
Figure 11:
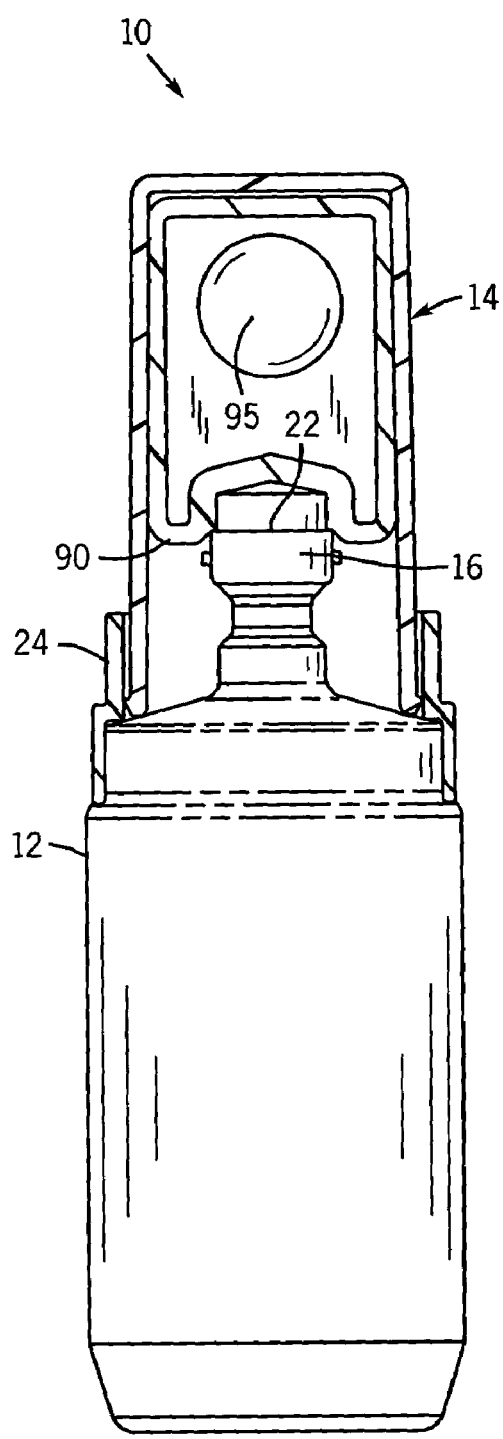
FIG. 11 is a partial sectional side view similar to FIG. 10, but the overcap and closure top have been rotated to fracture the first frangible seal.
Figure 12:
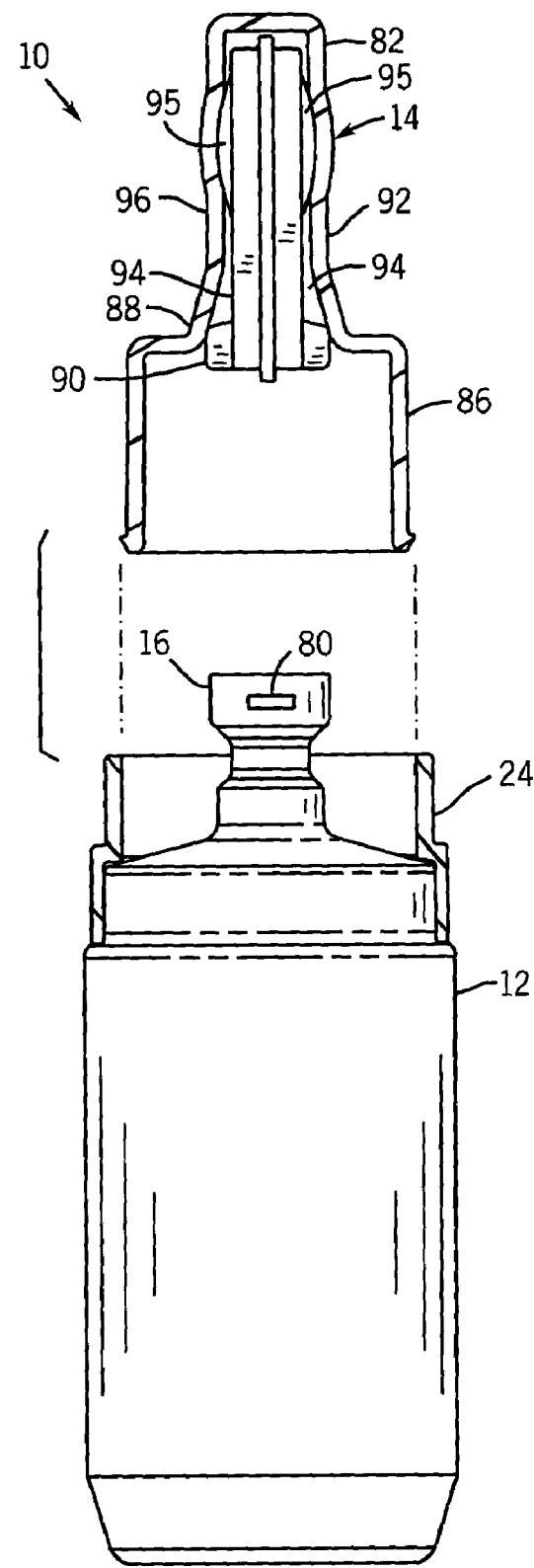
FIG. 12 is a partial sectional side view similar to FIG. 11, but the overcap and the closure top retained therein have been removed.

Referring to FIGS. 7, 10 and 12, a grip area 96 is located on the outer surface of upper cap 82 and at least forms a portion of the outer surface of detent portion 88. The grip area 96 permits a user to grasp and rock or rotate the upper cap 82. As the upper cap 82 is rotated, the mated detent portion 88 and closure top 90 twist relative to the container body 12. This rotation breaks the first frangible seal 22. Once the first frangible seal 22 is broken, the detent portion 88 and closure top 90 remain mated, and are removed from the container body 12. The closure top 90 is retained within the upper cap 82 once removed from the container body 12.

Figure 8:
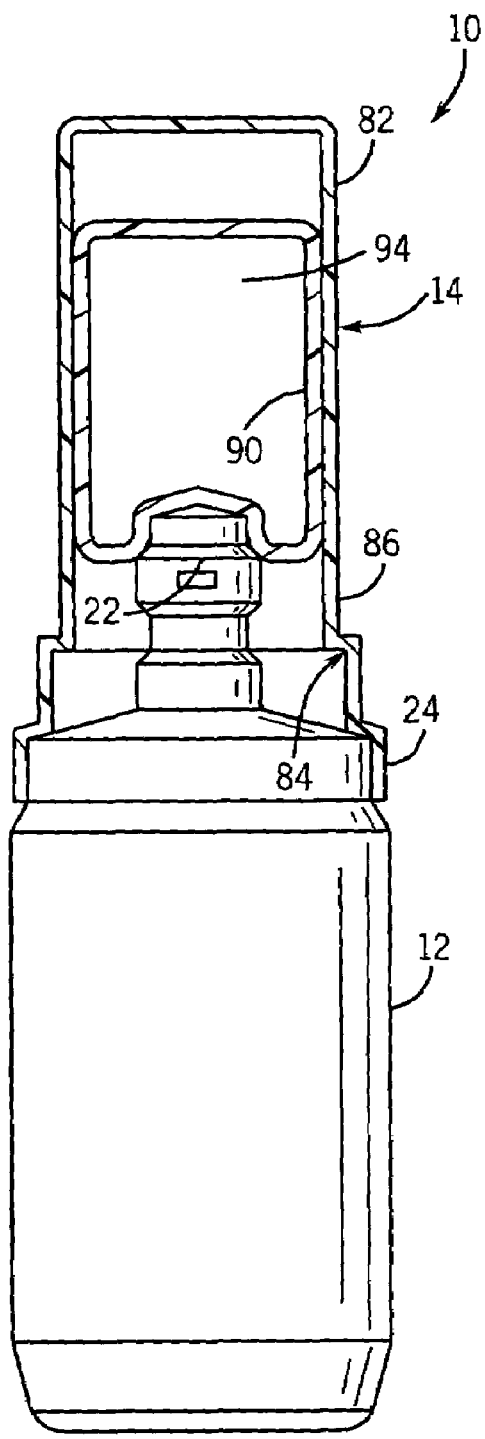
FIG. 8 is a partial sectional side view of the device of this invention taken on line 8—8 of FIG. 7.
Figure 9:
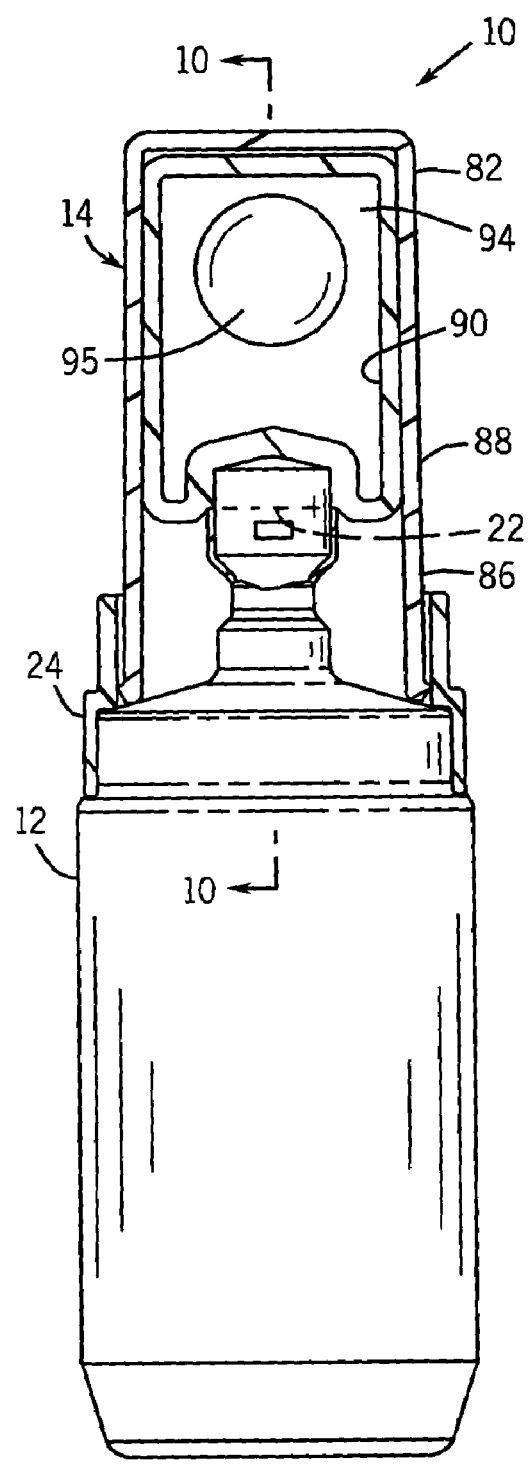
FIG. 9 is a partial sectional side view similar to FIG. 8, but the second frangible seal has been broken and the upper cap has been engaged with the closure top.

Referring to FIGS. 2 and 8, during formation, the container body 12 and closure top 20 or 90 are formed by a blow/fill/seal method and then sterilized. The material that forms the container body 12, the closure top 20 or 90, and the overcap 14 can be any material suitable for blow fill molding, and autoclave sterilization including but not limited to glass and plastic. More preferably, the material is polypropylene based or polyethylene tetrachloride-based. Most preferably, the material is a polypropylene random copolymer, such as Huntsman 23M2CS30A or Exxon Mobil 9122. The overcap 14 is fusion welded to the container 12. The container body 12 and overcap 14 assembly are then autoclaved to sterilize the entire container assembly 10. The overcap 14 is not fixed to the closure top 20 or 90 during autoclaving, permitting expansion at different rates and in different dimensions so as to prevent unnecessary strain on the container assembly 10. Once the entire container assembly 10 is sterilized, the overcap 14 preserves the sterility of first frangible seal 22. When the second frangible seal 42 or 84 is broken, a sterile uncontaminated port 16 remains until the closure top 20 or 90 is rotated by the overcap 14 and removed from the container 12.

It is therefore seen that the present invention provides a container assembly that maintains a sterile barrier or zone around the port until just prior to use. The present invention further provides a container assembly adapted for use with a syringe and which includes an overcap to facilitate removal of a closure top from the container with a twisting motion rather than the usual rocking motion that can lead to spillage and contamination by touch. The present invention also provides an overcap with an improved detent portion for engaging the closure top of a container.

It is therefore seen that this invention will accomplish at least all of its stated objectives.

We claim:

1. A container assembly, comprising:
   a container body adapted to contain fluid, including a port having an aperture therein;
   a closure top attached over the aperture of the container body with a first frangible seal; and
   an overcap positioned over the first frangible seal and sealed to the container body to provide a sterile barrier surrounding the first frangible seal;
   wherein the overcap includes a cap base sealed to the container body and an upper cap connected to the cap base by a second frangible seal, the second frangible seal is broken by manually depressing the upper cap toward the container body.

2. The container assembly of claim 1, wherein the upper cap is attached to the closure top after the second frangible seal is broken by depressing the upper cap toward the container body.

3. The container assembly of claim 1, wherein the overcap includes a detent portion for securing the closure top to the overcap once the second frangible seal is broken.

4. The container assembly of claim 3, wherein the overcap and secured closure top are removable from container body by twisting the overcap to break the first frangible seal.

5. The container assembly of claim 3, wherein the detent portion frictionally attaches the closure top to the overcap.

6. A container assembly for use with a needleless syringe having
   a luer end, comprising;
   a container body adapted to contain fluid, including a port having an aperture therein adapted for use with a luer end of a syringe;
   a closure top attached over the aperture of the container body with a first frangible seal; and
   an overcap including a detent portion for associating the overcap to the closure top to allow a user to break the first frangible seal and remove the closure top by twisting the overcap;
   wherein the overcap includes a cap base sealed to the container body and an upper cap connected to the cap base by a second frangible seal, the second frangible seal is broken by manually depressing the upper cap toward the container body.

7. The container assembly of claim 6, wherein the upper cap is attached to the closure top after second frangible seal is broken by depressing the upper cap toward the container body.

8. A container assembly, comprising:
   a container body adapted to contain fluid, including a port having an aperture therein;
   a closure top attached over the aperture of the container body with a first frangible seal; and
   an overcap positioned over the first frangible seal and hermetically sealed to the container body to provide a sterile barrier surrounding the first frangible seal;
   wherein the overcap includes a cap base sealed to the container body and an upper cap connected to the cap base by a second frangible seal.

* * * * *